United States Patent [19]

Sugaya

[11] Patent Number: 4,857,272
[45] Date of Patent: * Aug. 15, 1989

[54] CHEMICAL ASSAY SYSTEM

[75] Inventor: Fumio Sugaya, Asaka, Japan

[73] Assignee: Fuji Photo Film Co., Ltd., Kanagawa, Japan

[*] Notice: The portion of the term of this patent subsequent to Apr. 22, 2003 has been disclaimed.

[21] Appl. No.: 875,489

[22] Filed: Jun. 18, 1986

[30] Foreign Application Priority Data

Jun. 21, 1985 [JP] Japan .................. 60-135612

[51] Int. Cl.$^4$ ............................. G01N 35/04
[52] U.S. Cl. .................... 422/65; 356/418; 356/445; 436/46
[58] Field of Search .............. 422/64, 65, 67; 436/46; 356/244, 246, 445, 418

[56] References Cited

U.S. PATENT DOCUMENTS

| | | | |
|---|---|---|---|
| 3,918,910 | 11/1975 | Soya et al. | 422/67 |
| 4,058,367 | 11/1977 | Gilford | 422/63 |
| 4,263,256 | 4/1981 | Morle | 422/102 |
| 4,338,279 | 7/1982 | Orimo et al. | 422/65 |
| 4,430,299 | 2/1984 | Horne | 422/65 |
| 4,488,810 | 12/1984 | Hatanaka et al. | 422/64 |
| 4,584,275 | 4/1986 | Okano et al. | 436/46 |

Primary Examiner—Michael S. Marcus
Attorney, Agent, or Firm—Jules E. Goldberg

[57] ABSTRACT

A chemical assay system comprises at least one incubator having a plurality of slide receiving chambers each for receiving a chemical assay slide. The chambers are arranged in a row so that the chemical assay slides received in the chambers are arranged in a row in one plane and each chamber is provided with an opening for exposing the chemical assay slide received therein. A probe for projecting light onto the chemical assay slide and measuring the intensity of the light reflected from the chemical assay slide is provided to be movable along the row of the chemical assay slides to positions in front of one of the openings of the slide receiving chambers.

3 Claims, 4 Drawing Sheets

CHEMICAL ASSAY SYSTEM

BACKGROUND OF THE INVENTION

1. Field of the Invention

This invention relates to a chemical assay system, and more particularly to a chemical assay system in which material to be assayed is caused to act on an assay slide bearing thereon one or more reagent layers and incubated for a predetermined time, and then coloration (extent of dye formation) in the assay slide is optically measured and analyzed for qualitative and/or quantitative determination of a particular component or particular components in the material.

2. Description of the Prior Art

Qualitative and/or quantitative determination of a particular chemical component in a liquid sample is widely used in various industrial fields. Especially, in the fields of biochemistry and clinical medicine, quantitative determination of a particular chemical component or particulate substance in body fluids such as blood or urine is extremely important.

Recently, there has been put into practice a dry type chemical assay slide by which a particular chemical component or material component in a liquid sample can be determined by depositing a droplet of the liquid sample on the slide. Japanese Patent Publication No. 53(1978)-21677, Japanese Unexamined Patent Publication No. 55(1980)-164356, for example, are referred to. By using such chemical assay slides, liquid samples can be assayed more easily and more quickly in comparison to the conventional wet analyzing process, and accordingly, the chemical assay slide is conveniently used in medical facilities, laboratories and the like where a large number of samples must be assayed.

When a liquid sample is assayed using the chemical assay slide, a measured quantity of the liquid sample is deposited on the slide and the slide is held in an incubator for a predetermined time at a constant temperature to permit reaction to cause coloration, and then light including a wavelength selected previously depending on the components of the liquid sample and the reagents contained in the reagent layers on the slide is projected onto the slide to measure the reflection density thereof.

In case where a large number of samples are assayed, automatic and continuous assay is preferred. Therefore, there have been proposed various chemical assay systems in which analysis of samples can be automatically and continuously effected using the dry type chemical assay slides described above.

For example, in the system disclosed in Japanese Unexamined Patent Publication No. 56(1981)-77746, a plurality of the chemical assay slides are sandwiched between a pair of rotatable disks at regular intervals in a circumferential direction of the disks and held at an elevated constant temperature for incubation by heaters provided on the disks, and after incubation for a predetermined time, the rotatable disks are rotated to successively oppose the slides to a probe disposed below the disks. The probe projects irradiating light onto each slide opposed thereto and receives reflected light through an opening formed in the lower disk. Though being advantageous in view of the efficiency in analyzing numerous samples, the system is disadvantageous in that a complicated disk rotating system including a control system is required which adds to the manufacturing cost and the size of the overall system.

In the system disclosed in Japanese Unexamined Patent Publication No. 58(1983)-21566, a U-shaped transfer path is formed in an incubator, each of a plurality of the chemical assay slides is supported by a carrier of a predetermined shape and is successively transferred along the transfer path, and each chemical assay slide is subjected to measurement of the reflected light density by a probe disposed along the transfer path after incubation for a predetermined time during transfer along the transfer path. The system is also advantageous with respect to the efficiency in effecting analysis of a plurality of samples, but is disadvantageous in that a mechanism for transferring the carriers for supporting the slides along the transfer path is required which adds to the manufacturing cost and the size of the overall system. Further, the system is disadvantageous in that it is not suitable for measuring the reflected light density a plurality of times in order to detect the rate of change of the optical density.

Further, there has been known a chemical assay system in which a plurality of chemical assay slides are stacked in an incubator, and after a predetermined time, the slides are successively taken out from the lowermost one to be subjected to measurement of the reflected light density. This system is advantageous in that since the slides are stacked in the incubator, the incubator may be relatively small in size but involves a problem that gas formed by the reaction occuring in one slide during incubation affects the reaction occuring in the other slides, lowering the accuracy of assay. Further, this system is not suitable for measuring the reflected light density a plurality of times in order to detect the rate of change of the optical density since the slides must be successively taken out from the incubator when the reflected light density is measured. Accordingly, it is difficult to measure the reflected light density during incubation.

SUMMARY OF THE INVENTION

In view of the foregoing observations and description, the primary object of the present invention is to provide a chemical assay system which is small in size and simple in structure, and in which chemical assay can be quickly and continuously effected with a high accuracy.

In accordance with one aspect of the present invention, there is provided a chemical assay system comprising at least one incubator having a plurality of slide receiving chambers each for receiving a chemical assay slide, the chambers being arranged in a row so that the chemical assay slides received in the chambers are arranged in a row in one plane and each chamber being provided with an opening for exposing the chemical assay slide received therein; a slide insertion means which is movable bidirectionally with respect to the incubators such that any slide can be inserted into said slide receiving chambers independently of any other slide and a probe means for projecting light onto the chemical assay slide and measuring the density of the light reflected from the chemical assay slide, the probe means being movable along the row of the chemical assay slides to positions in which it is opposed to one of the openings of the slide receiving chambers to measure the reflected light density of the chemical assay slide received in the slide receiving chamber.

In accordance with another aspect of the present invention, the movable probe means is replaced by a fixed optic scanner having a plurality of parallelly disposed optic probes that are fixed in place and selectively activated to scan a respective slide.

DESCRIPTION OF THE PREFERRED EMBODIMENTS

Figure 5:
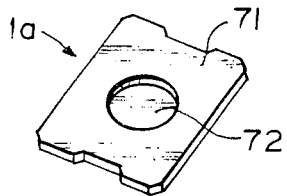
FIG. 5 is a perspective view showing the chemical assay slide.

In FIGS. 1 to 4, a first incubator 10 is provided with a plurality of (five in this particular embodiment) slide receivin chambers 11a to 11e arranged in a row in one plane. The slide receiving chambers 11a to 11e are adapted to receive therein chemical assay slides 1a to 1e. The first incubator 10 has a built-in heater (not shown) in order to incubate the chemical assay slides 1a to 1e respectively received in the slide receiving chambers 11a to 11e. Each of the chemical assay slides 1a to 1e comprises, as shown in FIG. 5, a dry type multi-layer assay film 72 housed in a frame 71 having a circular opening which gives access to the film 72 from opposite sides thereof. For example, a liquid sample is deposited on the film 72 through the opening from one side of the film 72 and irradiating light is projected onto the film 72 through the opening from the other side of the film 72 to conduct measurement of reflected light. The film 72 comprises a base sheet and a reagent layer and a spreading layer superposed on the base sheet in this order. A droplet of the liquid sample, e.g., urine or blood, is deposited on the spreading layer through the opening of the frame 71.

Figure 1:
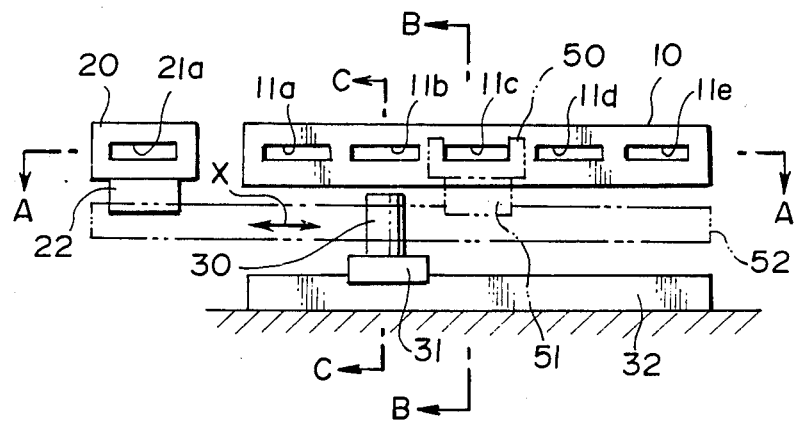
FIG. 1 is a schematic front view of a chemical assay system in accordance with an embodiment of the present invention.
Figure 2:
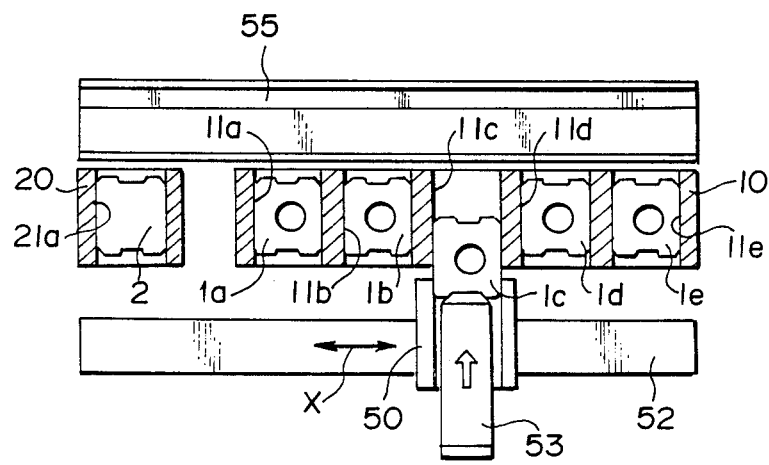
FIGS. 2 to 4 are cross-sectional views respectively taken along lines A—A, B—B and C—C in FIG. 1.
Figure 3:
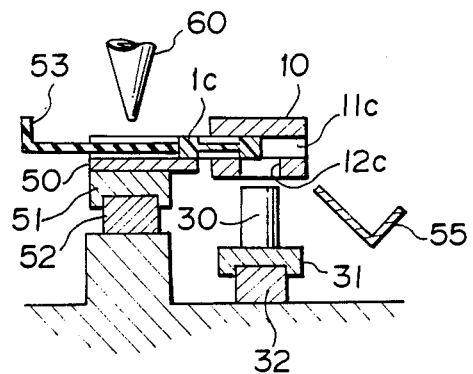
Figure 4:
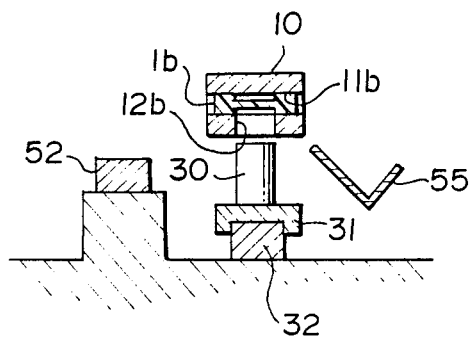

On the left (as seen in FIG. 1) side of the first incubator 10 is disposed a second incubator 20. The second incubator 20 is provided with a slide receiving chamber 21a which receives a chemical assay slide 2 to be aligned with the chemical assay slides 1a to 1e in the same plane. Both the first and second incubators 10 and 20 are fixedly mounted. The slides 1a to 1e in the first incubator 10 and the slide 2 in the second incubator 20 can be incubated at different temperatures.

In this particular embodiment, the slides 1a to 1e to be received in the first incubator 10 are for optically measuring the color reaction between the reagent layer and the component in the liquid sample for which the liquid sample is analyzed. On the other hand, the slide 2 to be received in the second incubator 20 is for measuring the ionic activity of a particular ion contained in the liquid sample by way of a potential difference generated in proportion to the logarithm of the ionic activity of the ion. Accordingly, the slide 2 comprises at least a pair of ion selective electrodes each having an ion selective outermost layer, and a capillary porous bridge extending between the ion selective electrodes. Control liquid is deposited on one of the ion selective electrodes and a sample liquid is deposited on the ion selective electrodes, and the potential difference between the electrodes is measured by an electrode head 22 mounted on the lower surface of the second incubator 20. Based on the potential difference, the ioninic activity of a specific ion in the sample liquid is determined according to a Nernst equation. In order to promote reaction of the sample liquid such as urine or blood, it is preferred that the first incubator be adapted to maintain the temperature of the slides 1a to 1e at a temperature substantially equal to the normal bodily temperature (about 37° C.), though the second incubator 20 need not be so and may be adapted to maintain the temperature of the slide 2 at about 30° C.

Below the first incubator 10 is disposed a probe 30 placed on a first linear motor comprising a first stator 32 and a first rotor 31 slidable on the first stator 32. The probe 30 is slid below the first incubator 10 in the direction of the row of the slides 1a to 1e by the first linear motor. The slide receiving chambers 11a to 11e in the first incubator 10 are respectively provided with openings 12a to 12e in the bottom surfaces thereof. The probe 30 is driven by the first linear motor so that the center of the probe 30 is brought into alignment with the center of the opening of one of the slides 1a to 1e respectively received in the slide receiving chambers 11a to 11e in order to measure the density reflected by the corresponding slide. In order to obtain a high accuracy of measurement, the center of the probe 30 must be precisely aligned with the center of the opening of the each slide. The linear motor is suitable for precisely locating the probe with respect to the slide.

The chemical assay slides 1a to 1e and 2 are respectively inserted into and discharged from the slide receiving chambers 11a to 11e and 21a by a guide rail 50 and an insertion/discharge lever 53. The guide rail 50 is moved along the row of the slide receiving chambers 11a to 11e by a second linear motr comprising a second stator 52 and a second rotor 51. When the guide rail 50 is positioned opposed to a blank slide receiving chamber 11 (11a to 11e) with a slide 1 (1a to 1e) placed thereon, the insertion/discharge lever 53 is actuated to insert the slide 1 into the blank slide receiving chamber. The amount of insertion of the insertion/discharge lever 53 into the slide receiving chamber is adjusted in advance to position the slide 1 in place in the slide receiving chamber. For discharging the slide 1 from the slide receiving chamber, the lever 53 is inserted home into the chamber to push the slide 1 outside the chamber onto a receiving plate 55 disposed on the opposite side of the lever 53.

Now, operation of the chemical assay system of this embodiment will be described, hereinbelow.

A chemical assay slide 1 is first placed on the guide rail 50 and the second linear motor is energized to move the guide rail 50 to bring the slide 1 thereon below a sample feed tip 60 which may be a tip of a micro pipette, a dropper cup, a nozzle or the like. Then a predetermined amount of a sample liquid is deposited on the spreading layer of the film 72 through the sample feed tip 60. Thereafter, the guide rail 50 is moved to a position opposed to a blank one of the slide receiving chambers 11a to 11e of the first incubator 10 and the slide insertion/discharge lever 53 is actuated to insert the slide 1 on the guide rail 50 into the blank slide receiving chamber 11. Then the slide 1 is incubated in the first incubator 10 to promote color-forming reaction between the sample liquid and the reagent layer of the slide 1. After incubation for a predetermined time, the first linear motor is energized to move the probe 30 to bring the center of the probe into alignment with the center of the opening of the slide 1, and then the irradiating light is projected to the slide 1 and the density of the reflected light is measured through the opening in the bottom surface of the slide receiving chamber 11. In this manner, the measurement of the reflected light density may be effected once after completion of the color-forming reaction or may be effected a plurality of times at predetermined intervals during progression of the color reaction in order to detect the rate of change of the reflected light density (rate assay method). In the latter case, the time the slide 1 in each slide receiving chamber 11 is memorized and the probe 30 is moved to be opposed to each slide at predetermined intervals after the slide is inserted in the first incubator 10. This is an easy operation. Further, since each slide receiving chamber 11 is isolated from the other chambers, gas discharged during the color reaction in each of the slides cannot affect the color reactions in the other slides.

When the slide 2 is inserted into the slide receiving chamber 21a of the second incubator 20, the guide rail 50 is moved to bring the slide 2 placed thereon below the sample liquid feed tip 60 and below a tip (not shown) for feeding the control liquid. After the sample liquid and the control liquid are deposited on the slide 2, the guide rail 50 is moved to a position opposed to the slide receiving chamber 21a and the slide 2 is inserted into the chamber 21a by the lever 53 in the manner described above. After incubation in the second incubator 20 for a predetermined time, the ionic activity of a desired ion is measured by the electrode head 22.

After completion of the measurement of each slide, the guide rail 50 is moved to the position opposed to the chamber corresponding to the slide and the slide insertion/discharge lever 53 is actuated to push out the slide onto the receiving plate 55.

In the embodiment described above, the second incubator 20 is arranged for measurement of ionic activity by the electrode head 22. However, it may be arranged for measurement of the reflected light intensity. In this case, the probe 30 is arranged to be slidable below the second incubator 20.

Figure 6:
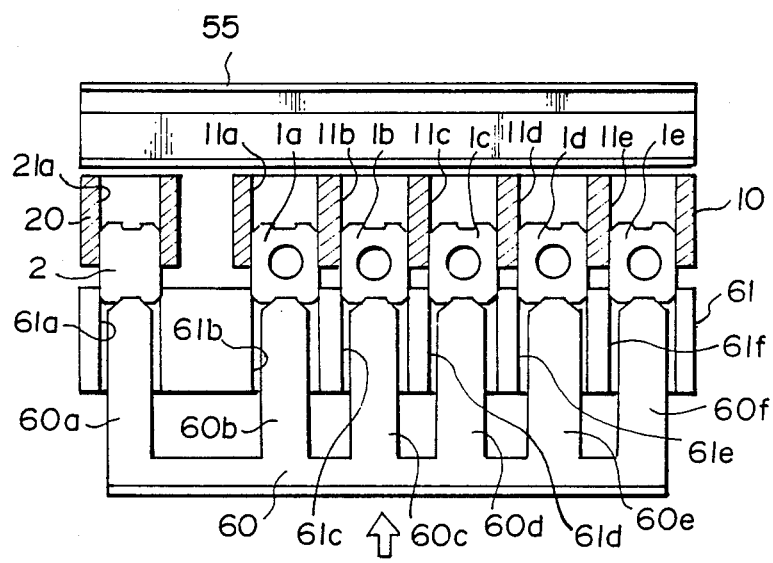
FIG. 6 is a plan view showing a chemical assay system in accordance with another embodiment of the present invention.

In the embodiment described above, the slides are successively inserted into or discharged from the slide receiving chambers by a combination of a single guide rail and a single lever slidable along the row of the chambers. However, the slides may be simultaneously inserted into or discharged from the chambers by a fixed guide rail 61 having a plurality of slide receiving grooves 61a to 61a respectively opposed to the chambers 21a and 11a to 11e, and an insertion/discharge lever 60 having a plurality of projections 60a to 60f adapted to push the slides in the respective slide receiving grooves 61a to 61f as shown in FIG. 6.

Figure 7:
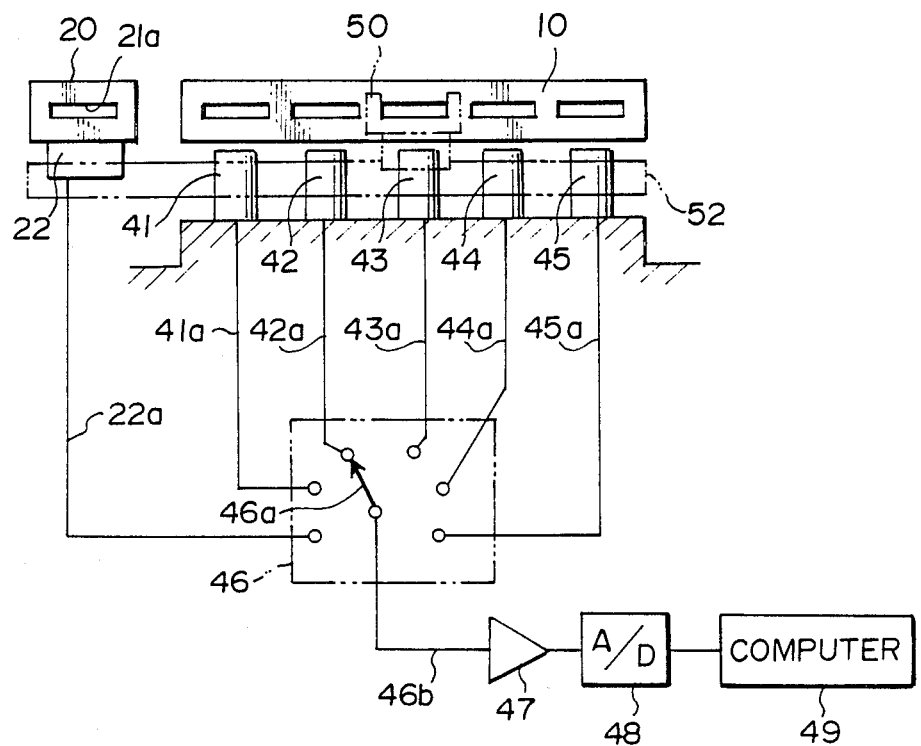
FIG. 7 is a schematic front view showing a chemical assay system in accordance with still another embodiment of the present invention.

FIG. 7 shows another embodiment of the present invention. The chemical assay system of this embodiment is very similar to the system shown in FIGS. 1 to 4 except that five probes 41 to 45 are provided each opposed to one of the slide receiving chambers 11a to 11e instead of the single probe 30 which is moved to be opposed to one of the chambers as required. That is, the probes 41 to 45 are fixedly provided to be respectively opposed to the chambers 11a to 11e and measure the reflected light intensity from the corresponding slides 1a to 1e in the chambers 11a to 11e. Output lines 41a to 45a of the respective probes 41 to 45 are connected to a scanner switch 46 to which also the electrode head 22 for measuring ionic activity is connected by way of an output line 22a. The scanner switch 46 has a movable contact 46a which is selectively brought into contact with one of the output lines 41a to 45a and 22a. An output line 46b connects the movable contact 46a to an amplifier 47. The output of the amplifier 47 is input into a computer 49 by way of an A/D converter 48. In this embodiment, by simply operating the scanner switch 46, any desired measurement can be effected.

As can be understood from the description above, in accordance with the present invention, the chemical assay system can be small in size and simple in structure, and measurement of the reflected light density and rate assay can be easily conducted separately from insertion of discharge of the chemical assay slides. Further, since the slide receiving chambers are separate from each other, gas formed in each slide during color-forming reaction therein cannot substanially affect color-forming reaction in the other slides.

I claim:

1. In a chemical assay system comprising at least one incubator having a plurality of slide receiving chambers each for receiving a chemical assay slide, the chambers being arranged in a row so that chemical assay slides received in the chambers are arranged in a row in one plane and each chamber is provided with an opening for exposing a chemical assay slide received therein; a slide insertion means for inserting chemical assay slides into the slide receiving chambers; and a probe means for projecting light onto a chemical assay slide in each slide receiving chamber and measuring the intensity of the light reflected therefrom, the probe means being movable along the row of the slide receiving chambers to measuring positions in front of each of the openings;

the improvement which comprises said slide insertion means being movable bi-directionally with respect to the incubators such that any slide can be inserted into said slide receiving chambers independently of any other slide.

2. A chemical assay system as defined in claim 1 in which said probe means is driven by a linear motor.

3. In a chemical assay system comprising at least one incubator having a plurality of slide receiving chambers each for receiving a chemical assay slide, the chambers being arranged in a row so that chemical assay slides received in the chambers are arranged in a row in one plane and each chamber is provided with an opening for exposing a chemical assay slide received therein; a slide insertion means for inserting chemical assay slides into the slide receiving chambers; and a probe means for projecting light onto a chemical assay slide in each slide receiving chamber and measuring the intensity of the light reflected therefrom, the probe means being movable along the row of the slide receiving chambers to measuring positions in front of each of the openings;

the improvement which comprises said slide receiving chambers and slide insertion means being arranged so that chemical assay slides are respectively and independently inserted into and discharged from each of the slide receiving chambers and wherein said probe means is replaced by a fixed optic scanner having a plurality of parallely disposed optics probes that are fixed in place and selectively activated to scan a respective slide and to measure the density of the light reflected from the chemical assay slide.

* * * * *